(12) United States Patent
Stidham et al.

(10) Patent No.: US 10,918,326 B2
(45) Date of Patent: Feb. 16, 2021

(54) AUTOMATED ASSESSMENT OF BOWEL DAMAGE IN INTESTINAL DISEASES

(71) Applicant: THE REGENTS OF THE UNIVERSITY OF MICHIGAN, Ann Arbor, MI (US)

(72) Inventors: Ryan W. Stidham, Ann Arbor, MI (US); Binu Enchakalody, Ann Arbor, MI (US); Mahmoud Al-Hawary, Ann Arbor, MI (US); Ashish Wasnik, Ann Arbor, MI (US); Stewart C. Wang, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 25 days.

(21) Appl. No.: 16/427,769

(22) Filed: May 31, 2019

(65) Prior Publication Data

US 2019/0365310 A1 Dec. 5, 2019

Related U.S. Application Data

(60) Provisional application No. 62/678,672, filed on May 31, 2018.

(51) Int. Cl.
*G06K 9/00* (2006.01)
*A61B 5/00* (2006.01)
(Continued)

(52) U.S. Cl.
CPC .......... *A61B 5/4255* (2013.01); *G06T 7/0012* (2013.01); *G06T 11/008* (2013.01); *G06T 7/10* (2017.01); *G06T 2207/30028* (2013.01)

(58) Field of Classification Search
CPC . A61B 18/1233; A61B 18/14; A61B 18/1482; A61B 18/16; A61B 2018/00023;
(Continued)

(56) References Cited

U.S. PATENT DOCUMENTS 9,723,971 B2 * 8/2017 Itai .................. G06T 7/0012
2007/0216678 A1 * 9/2007 Rouet .............. G06T 7/0012
345/423

OTHER PUBLICATIONS

Ryan W. Stidham, et al., Agreement of CT Imaging Features of Crohn's Disease Between Radiologists and Automated Machine Learning Image Analysis, Gastroenterology, Su1816 vol. 154, Issue 6, Supplement 1, May 2018, p. S-595.
(Continued)

*Primary Examiner* — Charlotte M Baker
(74) *Attorney, Agent, or Firm* — Harness, Dickey & Pierce, P.L.C.

(57) ABSTRACT

A computer-automated method is presented for segmenting image data for an organ of a subject, where the organ is a tubular structure. The method includes: receiving image data representing a volume of the subject, such that the image data includes the organ; generating a centerline through the organ; determining location of an outer wall of the tube within the image data, where the location of the inner wall is determined using the centerline; determining location of an outer wall of the tube within the image data, where the location of the outer wall is determined using the inner wall; and computing a measure of the organ from the image data.

19 Claims, 10 Drawing Sheets

(51) Int. Cl.
 *G06T 11/00* (2006.01)
 *G06T 7/00* (2017.01)
 *G06T 7/10* (2017.01)

(58) Field of Classification Search
 CPC ..... A61B 5/4255; A61B 5/1075; A61B 5/055; G06T 11/008; G06T 7/0012; G06T 2207/30028; G06T 7/10; G06T 2207/30172; G06T 2207/10081; G06T 2207/10088; G06T 7/12; G16H 30/40; G16H 50/20
 USPC .......................................... 382/131; 345/423
 See application file for complete search history.

(56) References Cited

OTHER PUBLICATIONS

Ryan W. Stidham, et al., Automated Image Analysis of CT Enterography Studies Predicts Future Surgery Similar to Experienced Radiologist Assessment in Small Bowel Crohn's Disease, Gastroenterology, Su1900 vol. 154, Issue 6, Supplement 1, May 2018, pp. S-625-S-626.

* cited by examiner

AUTOMATED ASSESSMENT OF BOWEL DAMAGE IN INTESTINAL DISEASES

CROSS-REFERENCE TO RELATED APPLICATIONS

This application claims the benefit of U.S. Provisional Application No. 62/678,672, filed on May 31, 2018. The entire disclosure of the above application is incorporated herein by reference.

GOVERNMENT CLAUSE

This invention was made with government support under K23DK101687 awarded by the National Institute of Health and W81XWH-16-1-0684 awarded by the Department of Defense. The government has certain rights in the invention.

FIELD

The present disclosure relates to automated assessment of bowel damage in intestinal diseases.

BACKGROUND

Inflammatory bowel disease (IBD), including Crohn's disease (CD) and ulcerative colitis (UC), may cause severe structural damage to small and large intestines. Structural damage is a result of intermittent periods of intestinal inflammation followed by healing, which if apparent, may result in substantial intestinal scarring. Intestinal scarring may lead to various forms of intestinal functional failure, intestinal strictures and stenoses, intestinal blockage, and spontaneous intestinal perforation that may require urgent surgery. Physicians face major challenges for deciding how to treat structural damage in patients, both at the time of diagnosis and over the course of the patient's lifetime. Measuring and monitoring structural damage more easily would allow physicians to make informative decisions about patients.

This section provides background information related to the present disclosure which is not necessarily prior art.

SUMMARY

This section provides a general summary of the disclosure, and is not a comprehensive disclosure of its full scope or all of its features.

A computer-automated method is presented for segmenting image data for an organ of a subject. The method includes: receiving image data representing a volume of the subject, such that the image data includes the organ; generating a centerline through of the organ; determining location of an outer wall of the tube within the image data, where the location of the outer wall is determined using the centerline; determining location of an inner wall of the tube within the image data, where the location of the inner wall is determined using the outer wall; and computing a measure of the organ from the image data.

In another aspect, a method for segmenting the organ is further described. The method includes: a) receiving image data of the organ of the subject, wherein the image data includes at least a small intestine of the subject; b) identifying an origin point within the image data, wherein the origin point is located at an intersection between the small intestine and a large intestine of the subject; c) generating a plurality of line segments that extend radially outward from the origin point, each line segment in the plurality of line segments terminates at an intersection with a first boundary of the organ; d) identifying a given line segment having longest linear dimension amongst the plurality of line segments; e) identifying a point along the given line segment to serve as a seed location; f) generating a plurality of additional line segments that extend radially outward from the seed location, each line segment in the plurality of additional line segments terminates at the intersection with the first boundary; and g) repeating steps d)-f) until the given line segment extends outside of the organ.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Measurements of intestinal inflammation may be performed using methods such as colonoscopy, computed tomography (CT) imagining, magnetic resonance imaging (MRI), and blood and stool biomarkers. However, performing measurements of structural damage in a small intestine (or bowel) of a subject may be time consuming, require experienced radiologists, and have limited reproducibility. Automated bowel morphomics (ABM) analyzes image data, such as a CT scan, MRI scan, or another type of scan, of an abdomen of the subject, and is able to segment the small intestine from the image data. Two three-dimensional structures representing the outer and inner wall (e.g., point cloud) of the small intestine may be generated. Measurements that are relevant to structural damage of the small intestine may be performed using the three-dimensional structure. A combination of these three-dimensional structures may also be used to compare subsequent scans of the subject or across a group of subjects.

Figure 1:
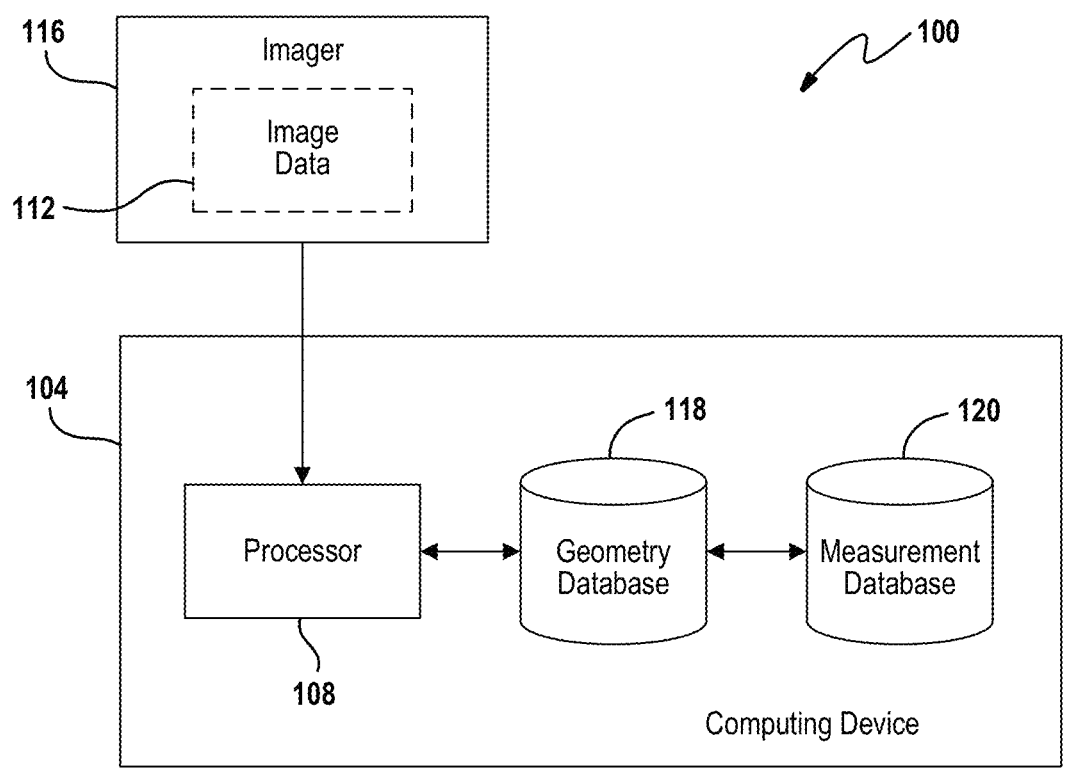
FIG. 1 is a block diagram illustrating an example automated bowel morphomics (ABM) system according to some embodiments of the present disclosure.

Referring now to FIG. 1, a block diagram illustrating an example automated bowel morphomics (ABM) system 100 is presented. The ABM system 100 includes a computing device 104 and an imager 116. The computing device 104 may be, for example, a laptop computer, personal computer (PC), etc. The computing device 104 may typically include a central processing unit (CPU) or processor 108 that analyzes image data 112, a geometry database 118 and a measurement database 120.

The imager 116 captures the image data 112 representing an organ of a subject. For example, the imager 116 may be a computed tomography (CT) machine, magnetic resonance imaging (MRI) machine, or another suitable image capturing machine. The image data 112 represents the organ of the subject and may include a plurality of cross-sectional image slices that collectively define the organ of the subject.

The processor 108 is configured to receive image data 112 from the imager 116. While one processor 108 is shown and discussed, the term processor may include two or more processors operating in parallel or in a distributed manner. The processor 108 may perform one or more measurements to analyze the image data 112, which is discussed further below.

The geometry database 118 is configured to store date (e.g., point cloud data) extracted from the image data, for example of the inner and outer wall of a small intestines. The measurement database 120 is configured to store the one or more measurements performed by the processor 108. These databases 118, 120 may include volatile or nonvolatile memory, cache, or other type of memory. The computing device 104 may include one or more additional components that are not shown (e.g., an input device, a display subsystem, or a network interface).

Figure 2:
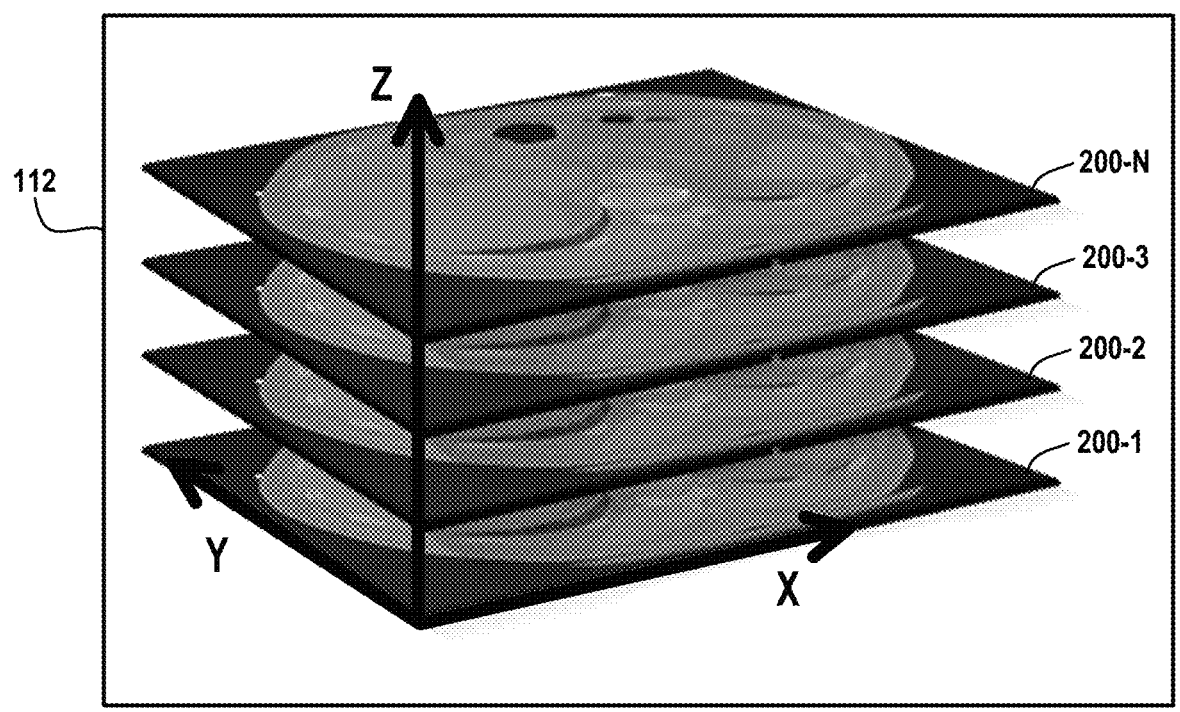
FIG. 2 is a schematic illustrating an example of image data including a plurality of image slices.

Referring now to FIG. 2, an exploded view of an example image data 112 is presented. The image data 112 includes N image slices, e.g., image slice 200-1, image slice 200-2, image slice 200-3 . . . image slice 200-N (individually referred to as image slice 200). In some embodiments, the image data 112 may be defined in a three-dimensional space, such that any point in the image data 112 may be referenced by an (x, y, z) coordinate. In the illustrated example, the z-coordinate may represent a particular image slice 200, and the (x, y) coordinates may represent a particular point in the particular image slice 200. In some embodiments, the (x, y) coordinates may refer to individual pixels in the image data 112. While the illustrated example references the image slice 200 by the z-coordinate, it should be appreciated that an image slice may be referenced by the x-coordinate or the y-coordinate. Furthermore, while a Cartesian coordinate system is described, it should be appreciated that other coordinate systems, such as polar coordinate systems may be used to segment the outer and inner wall perimeters while the coordinate system for the final saved image data 112 is in the Cartesian system.

As mentioned above, the image data 112 represents the organ of the subject. The organ of the subject may be a tube or tubularly shaped organ, such as a small intestine or a large intestine. It should be appreciated that the organ may include other types of tubular organs. For example, the organ may further include an esophagus or another organ from a gastrointestinal tract.

Referring back to FIG. 1, the processor 108 is further configured to analyze the image data 112 to identify one or more points within the image data 112. The processor 108 may identify one or more particular shapes of the organ, such that the one or more points in the image data 112 may be identified by the one or more particular shapes. In some embodiments, the one or more points may correspond to a potential origin point. In these embodiments, the processor 108 may analyze the image data 112 and assign a (0, 0, 0) coordinate to the potential origin point. For example, the one or more points may be located at one end of the tube representing an opening of the tube. More specifically, the one or more points may be located at an end where the small intestine intersects with the large intestine, referred to as an ileocolonic junction. In the example embodiment, the ileocolonic junction is the origin of the centerline. Any segment of the organ derived using this centerline is spatially and anatomically referenced as a distance from this origin. It should be appreciated that other shapes corresponding to the opening of the small intestine may be used. In some embodiments, a human user (e.g., technician) may identify one or more points located in the tube. While some components may be referenced using one or more points, other components may be referenced with one or more lines, curves, polygons, or other combinations thereof.

Figure 3:
FIG. 3 is a schematic illustrating a cross-sectional view of image data.

Referring now to FIG. 3, a cross-sectional view of the image data 112 is presented. The cross-sectional sagittal view is taken from a (y, z) plane of the image data 112. In the example of FIG. 3, the processor 108 has identified a plurality of points 300-1, 300-2, and 300-3, collectively referred to as points 300. The points 300 may be located at one end of the organ of the subject. For example, the points 300 may be located at an opening end of where the small intestine intersects with the large intestine, such that the points 300 may identify the shape of the intersection. The points 300 may be located inside the organ. For example, the points 300 may be located inside of a lumen of the small intestine. In some embodiments, the processor may determine the points 300 using deep learning analysis, such as deep neural networks, probabilistic atlas, or another suitable deep learning analysis.

One point of the plurality of points 300 may be designated as an origin point 300-3. The origin point 300-3 may be a point that has the highest likelihood of being located substantially near a center of a cross-section of the organ. The origin point 300-3 may have (0, 0, 0) coordinates.

Referring back to FIG. 1, once the processor 108 identifies an origin point, the processor 108 may generate a plurality of line segments that extend radially outward from an origin point and to the perimeter of the organ. For example, the plurality of line segments may extend in all directions (e.g., (x, y, z) directions) from the origin point and into the tube of the small intestine. Each line segment in plurality of line segments may terminate when an outer wall of the tube is detected. For example, each line segment in the plurality of line segments may terminate at an intersection between the corresponding line segment and the outer wall of the tube. The inner wall of the tube may be referred to as an additional boundary and is determined by going inward from the outer wall towards the center. In some embodiments, a random walk analysis is used to generate the plurality of line segments. The foregoing example of generating the plurality of line segments is not intended to be limiting and it should be appreciated that other methods may be used to generate the plurality of line segments. For example, the process may identify the inner wall of the tube first and, from the inner wall, identify the outer wall.

The processor 108 may detect the wall of the tube by comparing sudden changes in signal gradient over the mean signal. The gradient may include a magnitude of the image pixels brightness (e.g., measured in radiodensity or Hounsfield units) or other signal characteristics.

The processor 108 may, for example, identify a pixel of the origin point. The processor 108 may also identify an additional pixel located along each line segment in the plurality of line segments. The additional pixel along each line segment may include a change in brightness signal magnitude that may be quantified into a signal measurement unit (e.g., higher Hounsfield unit than the pixel of the origin point). The processor 108 may iteratively compare the signal magnitude of the additional pixel along each line segment with the pixel of the origin point until the magnitude of the additional pixel is greater than a predetermined amount. In some embodiments, the predetermined amount may be two or three standard deviations of the magnitude of the pixel at the origin point. The foregoing example of detecting the outer wall is not intended to be limiting and it should be appreciated that other methods may be used to detect the outer wall.

Once the processor 108 detects the outer wall of the tube, the processor 108 may determine a linear dimension of each line segment in the plurality of line segments. For example, the processor 108 may determine a length of each line segment in the plurality of line segments. The length of each line segment may be defined as a distance between the origin point and the intersection of each line segment with the outer wall of the tube. The processor 108 identifies a given line segment having the longest linear dimension amongst the plurality of line segments. The given line segment is retained and a plurality of additional line segments are generated from the given line segment, which is discussed further below. In some embodiments, each line segment may be ranked based on the length of the corresponding line segment and a confidence interval. The confidence interval may be based on an amount of variation in magnitude from a beginning to an end of the line segment, such that lower the variation in magnitude the higher the confidence.

Figure 4:
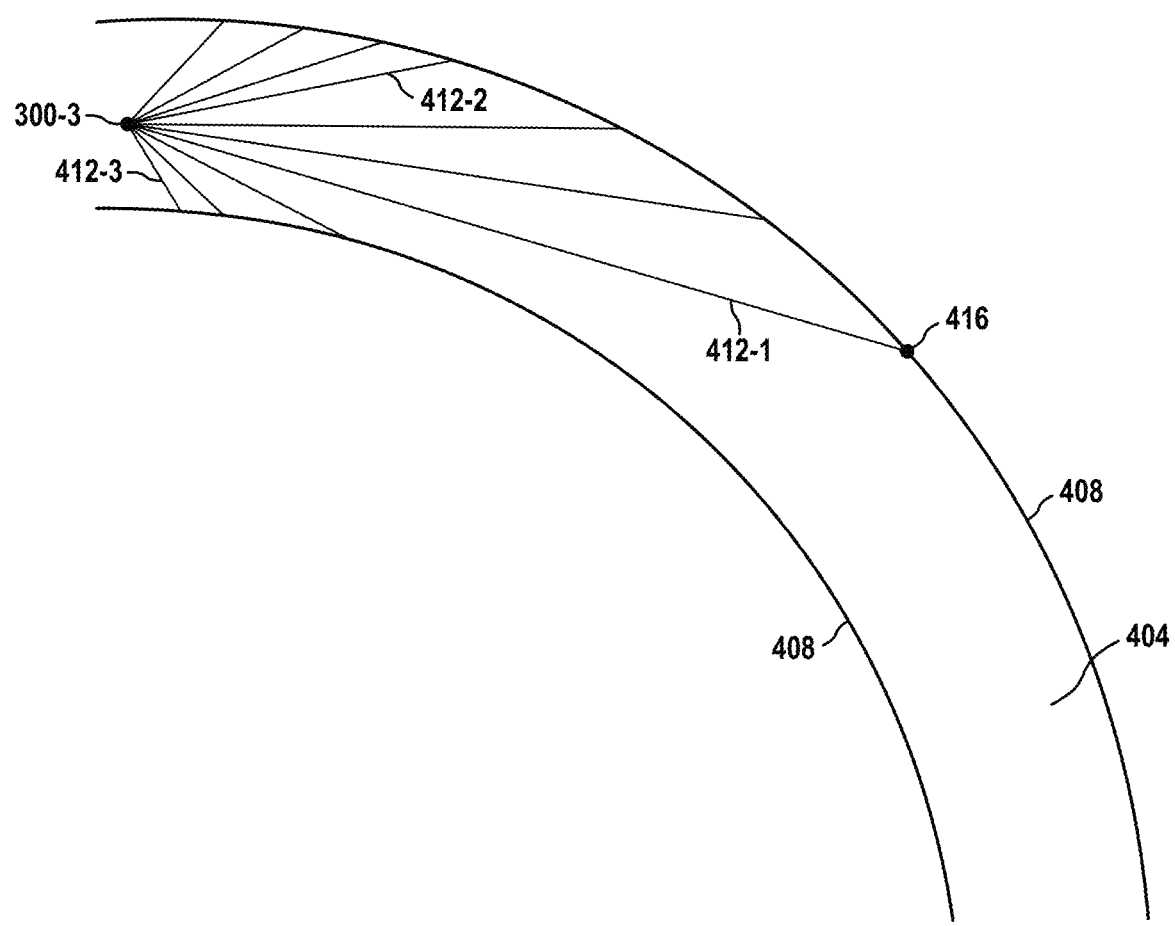
FIG. 4 is a schematic illustrating a cross-sectional view of a tube of an organ.

Referring now to FIG. 4, a cross-sectional view of a tube 404 of the organ is presented. The tube 404 may be defined by an outer wall 408. In the illustrated example, a plurality of line segments 412, e.g., 412-1, 412-2, and 412-3, are generated from the origin point 300-3. For example, the processor 108 may generate the plurality of line segments 412 that extend radially outward (e.g., (x, y, z) directions) from the origin point 300-3 and into the tube 404. Each line segment, e.g., 412-1, 412-2, and 412-3, may terminate at an intersection between the corresponding line segment and the outer wall 408. For example, the line segment 412-1 extends radially outward from the origin point 300-3 and terminates at an intersection 416. The intersection 416 may correspond to the intersection between the line segment 412-1 and the outer wall 408. While the illustrated example references the plurality of line segments 412 in two-dimensions, it should be appreciated that the plurality of line segments 412 extend in three-dimensions.

The outer wall 408 may be detected by comparing magnitude between the origin point 300-3 and magnitude of different points along each line segment, e.g., 412-1, 412-2, and 412-3. For example, the processor 108 may compare a signal magnitude of a pixel of the origin point 300-3 and a signal magnitude of an additional pixel located along the line segment 412-1. When the magnitude of the additional pixel along the line segment 412-1 is greater than a predetermined amount, the outer wall 408 is detected. For example, the predetermined amount may be two or three standard deviations of the signal magnitude of the pixel of the origin point. While the illustrated example references identifying a signal magnitude of an additional pixel located along the line segment 412-1, it should be appreciated that the additional pixel may be located along any one of the plurality of line segments 412.

Once the outer wall 408 is detected, a linear dimension of each line segment, e.g., 412-1, 412-2, and 412-3 is determined. For example, the processor 108 may determine a length of each line segment, e.g., 412-1, 412-2, and 412-3. A given line segment having the longest linear dimension amongst the plurality of line segments 412 is identified. In the example of FIG. 4, the line segment 412-1 has the longest length.

Referring back to FIG. 1, once the given line segment having the longest linear dimension is retained, the processor 108 may generate a plurality of additional line segments from an end point of the given line segment. The plurality of additional line segments may be generated in a similar manner as described above, except that the plurality of additional line segments extend radially outward (e.g., (x, y, z) directions) from a terminus of the given line segment rather than from an origin point. The terminus may correspond to the end point of the given line segment. For example, the terminus of the given line segment may be the intersection of the given line segment with the outer wall of the tube. Each line segment in the plurality of additional line segments may terminate when the outer wall of the tube is detected. For example, each line segment in the plurality of additional line segments may terminate at an intersection between the corresponding line segment and the outer wall of the tube. The foregoing example of generating the additional line segments is not intended to be limiting and it should be appreciated that other methods may be used to generate the additional line segments.

In some embodiments, the processor 108 may generate a plurality of additional line segments from a seed point. The seed point may be located anywhere along the given line segment including at a midpoint, a point between the midpoint and an endpoint, or at another predetermined location along the given line segment.

Similar to above, the processor 108 may detect the outer wall of the tube by comparing gradient change (e.g., pixel brightness) between pixels. For example, the processor 108 may compare a signal magnitude of a pixel of the terminus with a signal magnitude of an additional pixel located along each line segment. The processor 108 may iteratively compare the signal magnitude of the additional pixel along each line segment with the gradient of the pixel of the terminus until the magnitude of the additional pixel is greater than a predetermined amount.

The processor 108 may further identify a given line segment having the longest linear dimension amongst the plurality of additional line segments. The processor 108 may iteratively generate a plurality of additional line segments from a terminus of a given line segment and identify a given line segment until the given line segment extends outside of the tube like shaped organ. The given line segment may extend outside of the tube when an end (e.g., opposite to the end of where the origin point is located) is reached. For example, the given line segment may extend outside of the tube at an intersection between the small intestine and a stomach.

Figure 5:
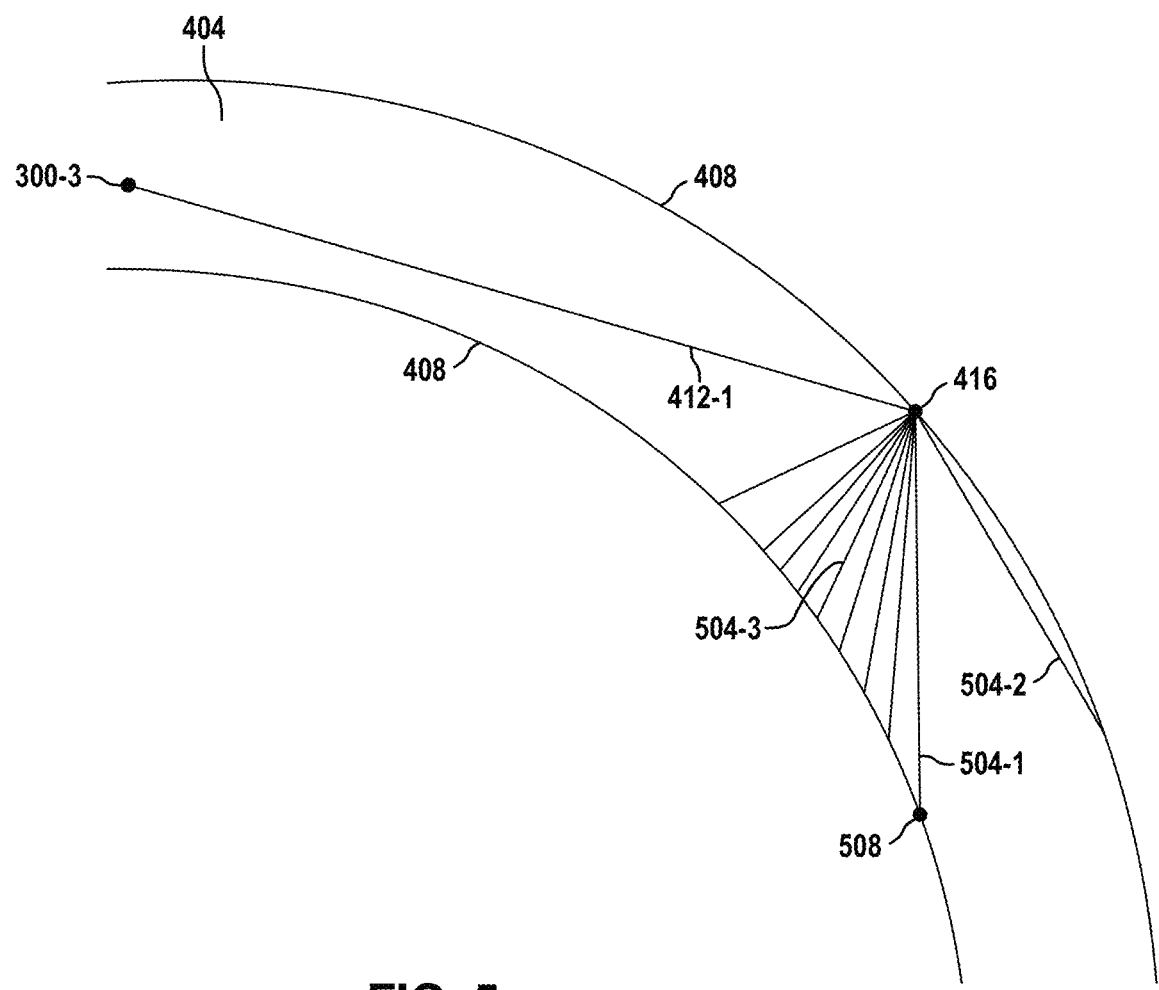
FIG. 5 is a schematic illustrating an example of generating a plurality of additional line segments in relation to the cross-sectional view of the tube like shaped organ of FIG. 4.

Referring now to FIG. 5, a plurality of additional line segments 504, e.g., 504-1, 504-2, and 504-3, may be generated from the intersection 416. In the example of FIG. 5, the intersection 416 may be referred to as a terminus 416 of the given line segment 412-1. The plurality of additional line segments 504 extend radially outward (e.g., (x, y, z) directions) from the terminus 416 and into the tube 404. Each line segment, e.g., 504-1, 504-2, and 504-3, may terminate at an intersection between the corresponding line segment and the outer wall 408. For example, the line segment 504-1 extends radially outward from the terminus 416 and terminates at an intersection 508. The intersection 508 may correspond to the intersection between the line segment 504-1 and the outer wall 408. While the illustrated example references the plurality of additional line segments 504 in two-dimensions, it should be appreciated that the plurality of additional line segments 504 extend in three-dimensions.

Similar to the example presented in FIG. 4, the outer wall 408 may be detected by comparing contrast between the terminus 416 and along each line segment, e.g., 504-1, 504-2, and 504-3. For example, the processor 108 may compare a magnitude of a pixel of the terminus 416 with a magnitude of an additional pixel located along the line segment 504-1. When the signal magnitude of the additional pixel along the line segment 504-1 is greater than a predetermined amount, the outer wall 408 may be detected. For example, the predetermined amount may be two or three standard deviations of the signal magnitude of the pixel of the terminus 416. While the illustrated example references identifying a signal magnitude of an additional pixel located along the line segment 504-1, it should be appreciated that the additional pixel may be located along any one of the plurality of additional line segments 504.

Once the outer wall 408 is located, a linear dimension of each line segment, e.g., 504-1, 504-2, and 504-3 is determined. For example, the processor 108 may determine a length of each line segment, e.g., 504-1, 504-2, and 504-3. A given line segment having the longest linear dimension amongst the plurality of additional line segments 504 is identified and retained. In the example of FIG. 5, the line segment 504-1 has the longest length. The processor 108 may iteratively generate a plurality of additional line segments from a terminus of a given line segment and identify a given line segment until the given line segment extends outside of the organ. For example, the given line segment may extend outside of the tube 404 at an intersection between the small intestine and the stomach.

Referring back to FIG. 1, once the processor 108 determines that the given line segment extends outside of the tube, the processor 108 may generate a centerline through the tube like shaped organ of the subject. The processor 108 may generate the centerline, for example, by joining the given line segments together to form a spline curve (e.g., non-linear best-fit line). The centerline provides a reference for the location of the tube. The centerline is generally located in a center of a cross-section of the tube. The foregoing example of generating the centerline is not intended to be limiting and it should be appreciated that other methods may be used to generate the centerline.

Figure 6A:
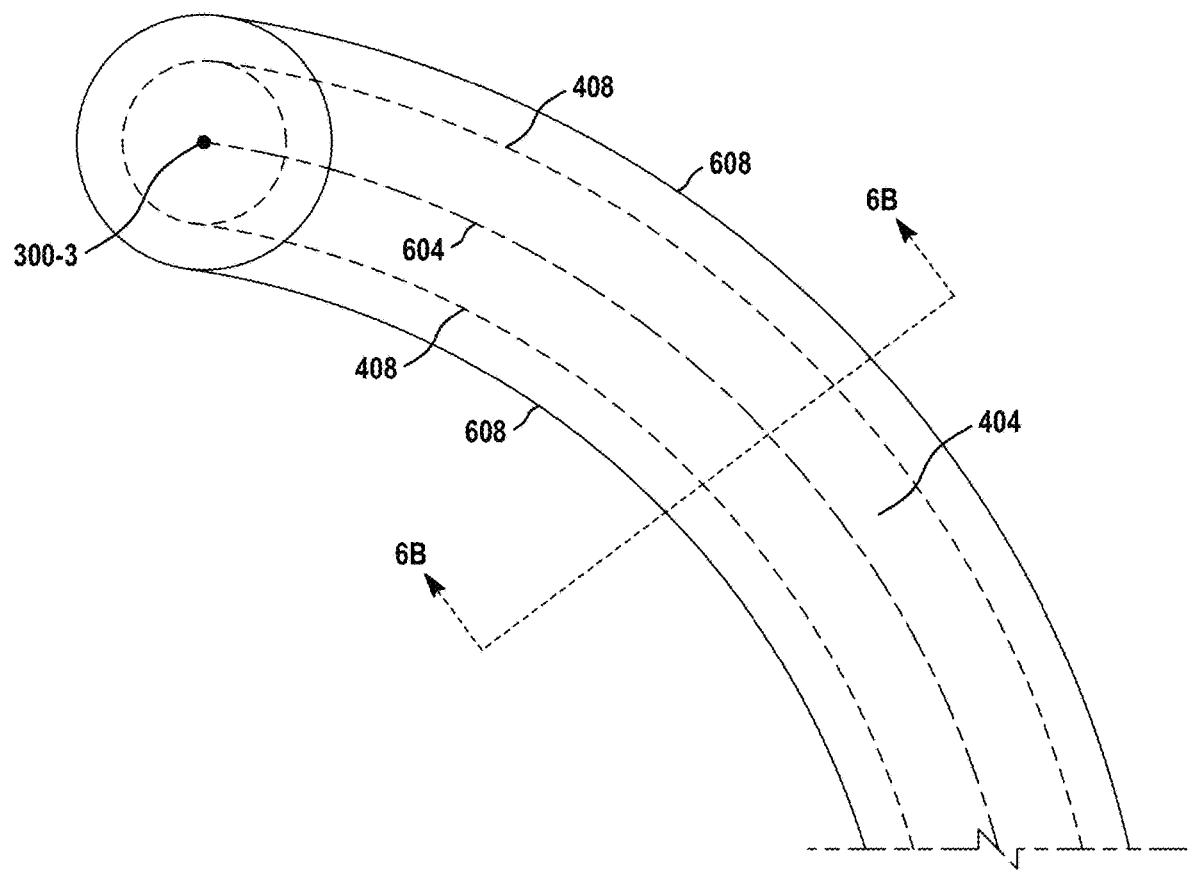
FIG. 6A is a schematic illustrating a perspective view of an organ of a subject.
Figure 6B:
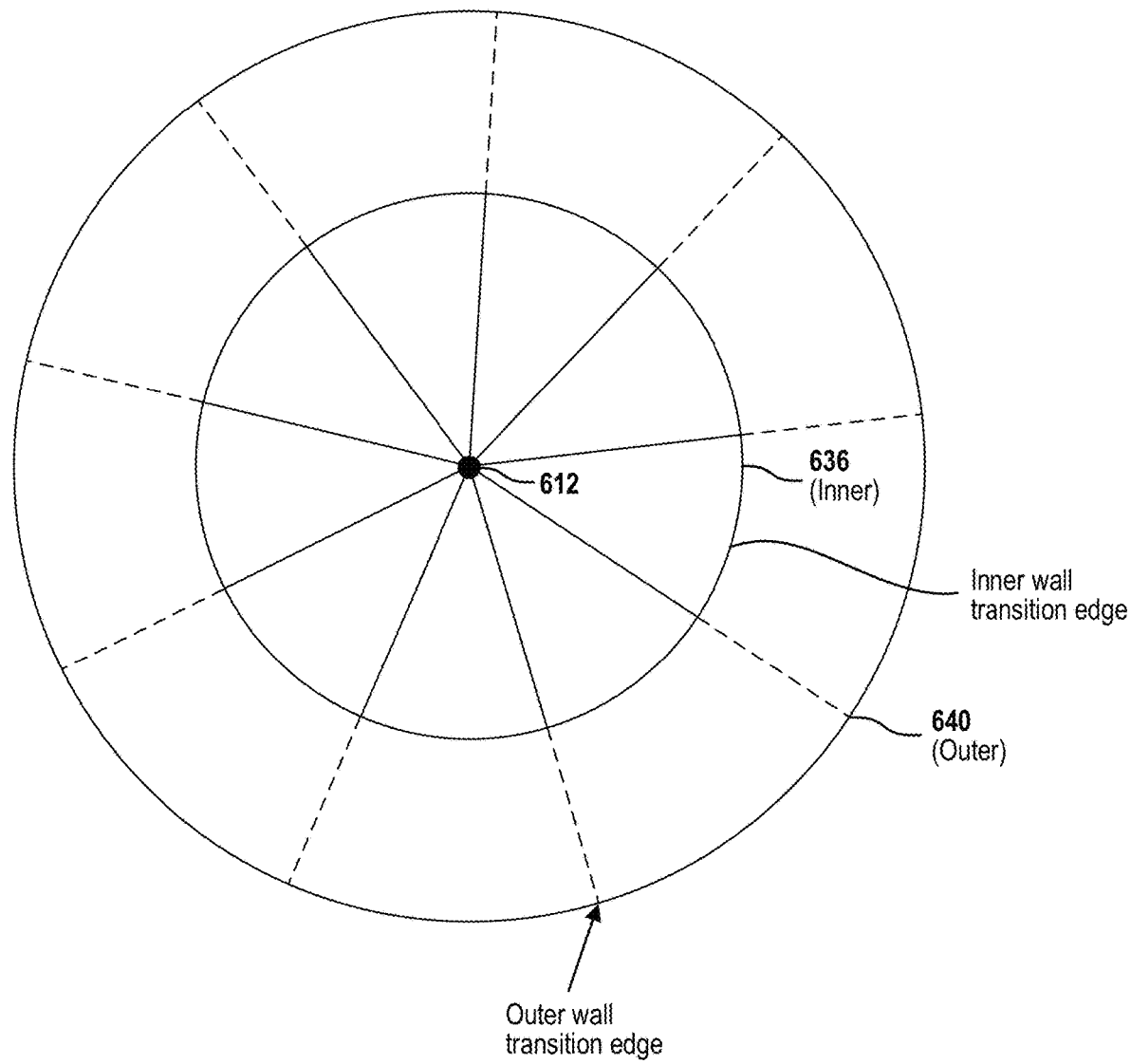
FIG. 6B is a schematic illustrating a cross-sectional view of the organ of the subject taken along line 6B-6B of FIG. 6A.

With reference to FIG. 6B, the processor 108 may also determine a location of an inner wall using a method similar to that of determining the location of the outer wall as described above. The processor 108 may generate a plurality of inner wall line segments that extend radially inward from the outer wall 640. The plurality of inner wall line segments extend in a direction that is orthogonal (e.g., 90 degrees) to the outer wall. Each line segment in the plurality of inner wall line segments may terminate when an inner wall of the tube is detected. For example, each line segment in the plurality of inner wall line segments may terminate at an intersection between the corresponding line segment and the inner wall of the tube. The foregoing example of determining the location of the inner wall is not intended to be limiting and it should be appreciated that other methods may be used to determine the location of the inner wall.

The processor 108 may detect the inner wall of the tube by comparing signal magnitude between the second seed point and data points along each line segment in the plurality of inner wall line segments. For example, the processor 108 may compare a signal magnitude of a pixel of the second seed point with a signal magnitude of an additional pixel located along each line segment. The processor 108 may iteratively compare the signal magnitude of the additional pixel along each line segment with the signal magnitude of the pixel of the second seed point until the signal magnitude of the additional pixel is greater than a predetermined amount. In some embodiments, the predetermined amount may be two or three standard deviations of the signal magnitude of the pixel of the second seed point. The inner wall of the tube may also be referred to as a second boundary.

The processor 108 may identify an endpoint associated with each line segment in the plurality of inner wall line segments and the endpoint may be located at the intersection between the corresponding line segment and the inner wall of the tube. The processor 108 may generate an inner wall line by joining the endpoints of each line segment in the plurality of inner wall line segments using, for example, a spline curve. The inner wall line is approximately parallel to the outer wall line.

As mentioned above, the centerline is generally located in the center of the cross-section of the tube. In some embodiments, a human user (e.g., technician) may edit the centerline such that the centerline is located approximately in the center of the tube. In some additional embodiments, the centerline may not be in the exact center of the tube. In these embodiments, the centerline may be located anywhere within the tube.

Referring now to FIG. 6A, a schematic of the organ of the subject is presented. In the example of FIG. 6A, the processor 108 has generated a centerline 604 by joining the given line segments. These line segments are interpolated, smoothed and undergoes post processing to form a spline curve. The centerline 604 may start at the origin point 300-3 and is generally located in a center of a cross-section of the tube 404. In some embodiments, the centerline may not be in the exact center of the tube. In these embodiments, the centerline may be located anywhere within the tube. A bowel wall is defined as the portion located between the inner wall 408 and an outer wall 608. Mesenteric fat and extra-intestinal structures are located outside of the outer wall 608.

Another approach for detecting the outer and inner walls is presented below. In this approach, an interpolated centerline using the center points is used to create a straightened, curved planar reformation (CPR) of the segment. Thereby reconstructing the originally convoluted segment into a sub-sampled, tubular version with the centerline as the center of its volume.

The coordinate system for each reconstructed cross-sectional slice is mapped from Cartesian to Polar coordinates. This view can be described as "onion-peeling" the outer wall from its perimeter to the center point line. In this perspective of the segment, the center line is the new image origin and radial views from the center show the transitions between lumen, inner, outer bowel wall as almost parallel lines. For each radial profile, the outer wall transition edge candidates that exceed a pre-determined magnitude threshold are identified. Each profile can have multiple candidates based on the image location and signal magnitude. In order to eliminate unlikely edge candidates, a best-fit polynomial grid is iteratively modelled on these transition edges. The optimized, final grid is then remapped as the outer wall point cloud in Cartesian coordinates. The centerline and CPR is re-computed using the centroids of the newly fitted outer wall.

This process of transforming the segment from a Cartesian to Polar coordinate system is then repeated using a refined centerline to determine the transition edges of the inner wall. Here all voxels outside the outer wall are excluded. The inner wall transition edge candidates that exceed a pre-determined magnitude threshold are identified for each profile. The unlikely edges are eliminated by iteratively modelling a best-fit polynomial grid on these inner wall transition edges. The optimized, final grid gets remapped as the inner wall point cloud in Cartesian coordinates. The main intent of delineating an inner wall is to avoid misclassification of stratified bowel as lumen.

Segmentation failure for the inner and outer grid typically happens in scans with poor contrast between inner and outer wall transition.

The volume within the inner wall is pre-processed to accommodate an expected range of voxel signal. Using super-pixel voxel segmentation followed by k-means classification, each pixel within the inner wall is segmented into one of two classes—lumen or non-lumen. Morphological operations are conducted on a lumen centric reconstructed volume to connect the segments.

Using the outer wall and lumen masks, the wall-thickness volume is measured by excluding the lumen from the outer wall volume. Descriptive 1-D, 2-D and 3-D, density-based, geometry-based and texture-based statistics can be derived from the bowel, wall thickness and lumen, volumes and masks. Measures taken at any location along the centerline have a spatial reference from the first centerline seed point. Example of geometry based descriptive statistics include equivalent radius/diameter, maximum, minimum, median, mean radius and diameter.

Because of the irregular shape of intestine (e.g. an imperfect ellipse), the equivalent radius or diameter is used to measure the total cross-sectional area. Examples of density based measures like maximum, minimum, mean, median density (e.g Hounsfield units in CT modality) for bowel, lumen volume and area.

An alternative approach to detecting the outer and inner walls can be done using a deep-convolutional neural network (D-CNN) model. The train set includes sub-sampled, cross-sectional images extracted at fixed intervals from the reconstructed volume. The corresponding label mask includes the outer, inner and lumen wall masks. This uses ~3000 data samples and augmented samples derived from 50 unique bowel segments. A two-dimensional, semantic segmentation model is trained to segment four classes—outer, inner wall, lumen wall and background. Background class includes all pixels outside of the outer wall perimeter. The output of the trained model is a probabilistic mask for four classes. The trained 2-D model is used to predict the outer and inner wall masks at regular intervals throughout the new segment. These masks can be converted into inner and outer cloud points which can use to derive measures from the segment.

Figure 7:
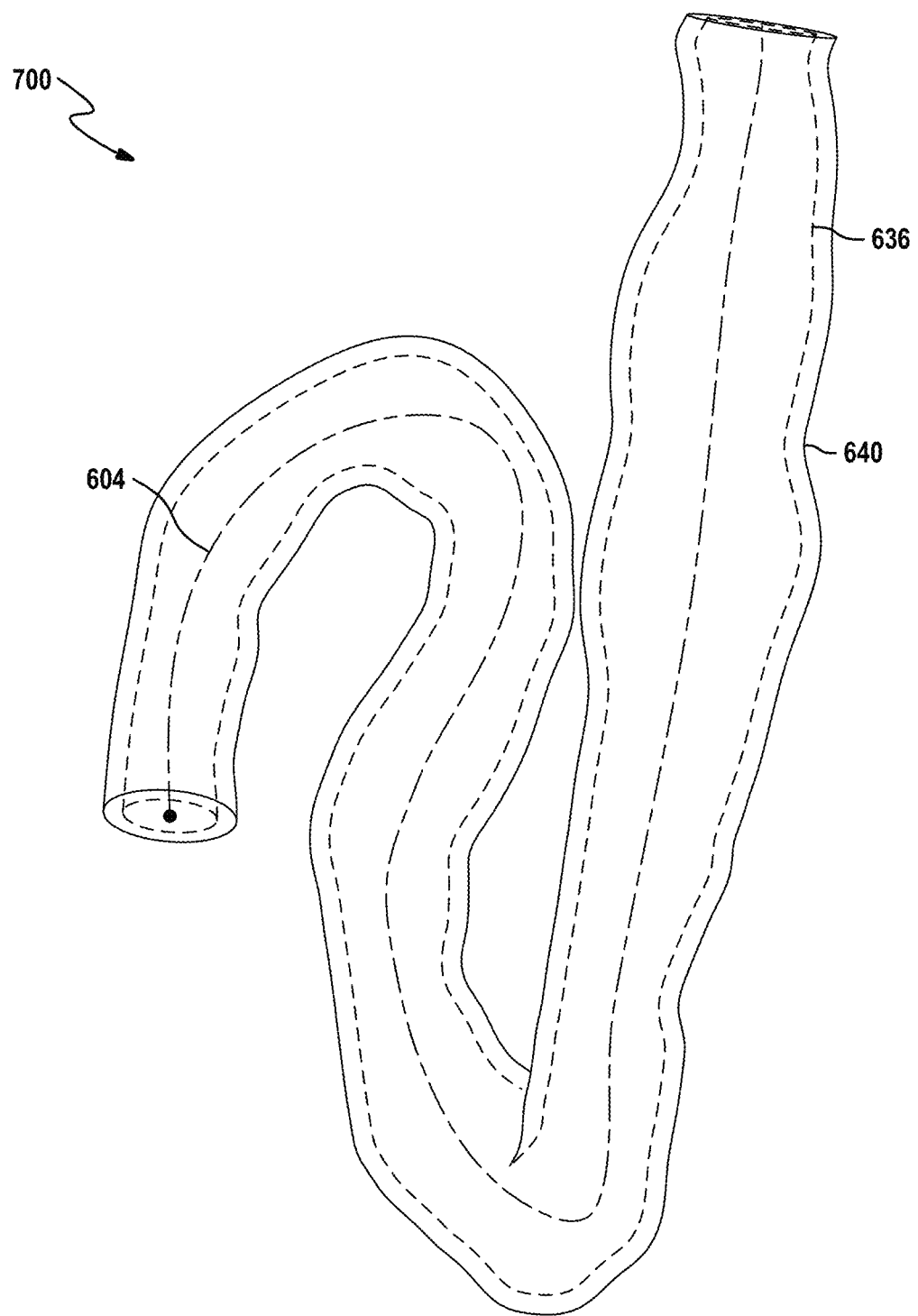
FIG. 7 is a schematic illustrating a three-dimensional structure of an organ of a subject.

Referring now to FIG. 7, a three-dimensional structure 700 of the organ of the subject is presented. The three-dimensional structure 700 may include a wire frame of the small intestine. The three-dimensional structure 700 may be generated, for example, by the processor 108 based on the centerline 604, the inner wall line 636, and the outer wall line 640. These three-dimensional structures 636 and 640 are saved in the geometry database 118 which is then used to compute one or more measurements of the small intestine.

The processor 108 may compute the one or more 1D, 2D, 3D geometry, density and texture based measurements derived from the inner outer wall point cloud and centerline points. Subsequently, a broad spectrum of anatomic measures can be derived to describe the bowel or another tubular organ. Any geometric description of the intestine can be acquired using the discussed bowel segmentation techniques, with clinically relevant examples including but not limited to bowel wall thickness, lumen diameter, length of disease, total bowel diameter, etc. Other examples include but are not limited to bowel wall and bowel lumen radius, diameter, cross sectional area, and volume calculations with descriptive statistics including minimum, maximum, mean, and median values with standard deviations. The one or more measurements may further include a diameter of the tube, diameter of the outer wall, length of a diseased section, and contrast assessment. Contrast assessment may include relative contrast enhancement of bowel wall or mucosal, bowel textural analysis, mesenteric fat stranding, and volumetric assessment. However, other measures of intestinal structure and characteristics not presently used in clinical care can be calculated by the bowel morphomics methods. First, cross sectional area of the lumen and bowel wall can be calculated, with descriptive statistics including minimum, maximum, variance, standard deviation, shape eccentricity and entropy, etc. Similar measures can also be calculated for bowel structure volumes. Second, the slope of linear, cross sectional or volumetric measurement change over the length of bowel can also be calculated to reflect disease characteristics. Third, relativistic measurements of bowel area and volume statistics as a ratio of diseased bowel compared to normal bowel can be performed to provide intra-individual standardization within an individual patient or scan.

Relative contrast enhancement is a median contrast enhancement of the bowel wall in the diseased section relative to the median contrast enhancement of the bowel wall from an upstream (or proximal) normal section separated by 5 centimeters from the diseased section. Relative contrast enhancement may include identifying a diseased and non-diseased intestine. For example, a trained, supervised learning classifier using a combination of bowel density, geometry and density predictors may be used to identify the diseased and non-diseased intestine. Alternatively, an unsupervised classifier using CNN methods can also be trained to achieve the same using expert-validated, equally spaced, diseased and non-diseased segments. Once the diseased section is identified, a comparable normal section of the bowel is identified for comparison. The normal section of bowel is the same length as the diseased section but 5 centimeters upstream from a proximal end of the diseased section. The median contrast enhancement (e.g. in CT modality Hounsfield units) are measured in the entire volume of the diseased section and the normal comparison section. A relative contrast assessment value may be calculated from the median contrast enhancement. The relative contrast assessment value is a ratio of the diseased to normal median enhancement within a volume, not cross-sections. By using the normal section of the bowel, technical differences between machines, protocol techniques, scan and contrast timing, etc. may be accounted for.

Bowel wall and lumen texture analysis includes using methods like gray level co-occurrence mapping (GLCM), gray level size zone matrix (GLSZM), Gray Level Zone Length Matrix (GLZLM) and Gabor filters. Bowel texture analysis may be done using a combination of local statistical descriptors derived from these matrices. e.g. homogeneity, contrast, energy, etc. This can provide a means to quantify signal heterogeneity and stratification.

Once the three-dimensional structure 700 is segmented, the organ may be mapped with one to one spatial fidelity to the true-space location of the organ in the image data 112. Since the organ may be mobile and position may vary between studies for a subject or between different subjects, linearization of the organ is helpful for comparing different image data. Linearization of the organ includes fitting the organ (e.g., small intestine) into a straight tube, aligned by an origin point. Spatial data is not lost during the linearization of the organ.

Figure 8:
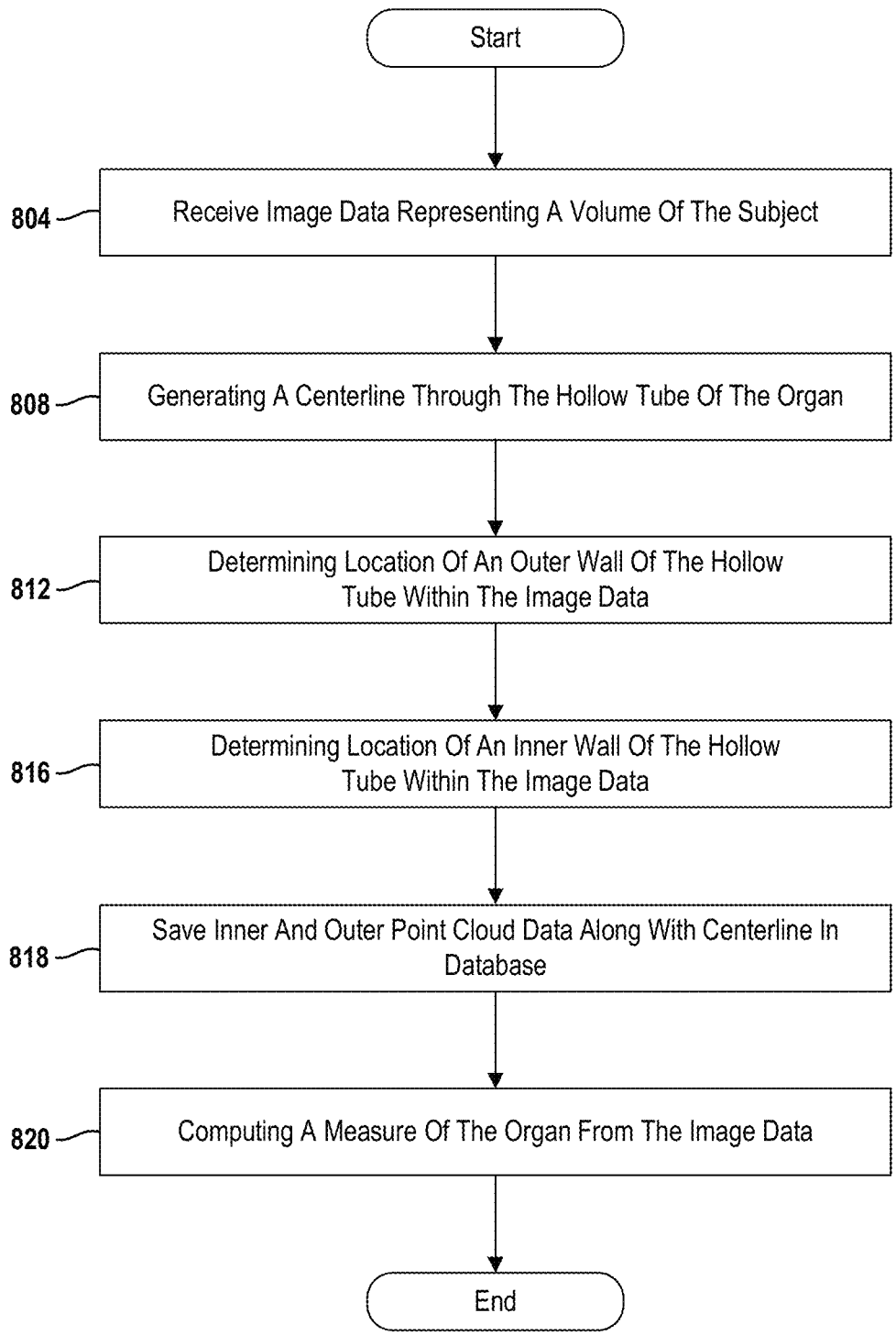
FIG. 8 is a flowchart illustrating an exemplary method for segmenting image data.

Referring now to FIG. 8, a flowchart illustrating an exemplary method for segmenting image data 112 is presented. Control beings at 804, where the processor 108 receives image data 112 representing an organ of a subject. For example, the organ of the subject may be a tube organ (e.g., small intestine). Control continues to 808 where upon receiving the image data 112, the processor 108 may generate a centerline (e.g., centerline 604) through the tube of the organ, which is described further below.

Control continues to 812 where, after the centerline is generated, the processor 108 may determine location of an outer wall of the tube within the image data 112. As described above, the processor may identify a first seed point within the image data 112. The first seed point may be located on the centerline. The processor 108 may generate a plurality of outer wall line segments that extend radially outward from the first seed point. The plurality of outer wall line segments extend in a direction that is orthogonal (e.g., 90 degrees) to the centerline. Each line segment in the plurality of outer wall line segments terminates at an intersection with the outer wall. To determine the intersection, the processor 108 may identify a magnitude of brightness of a pixel of the first seed point and identify a magnitude of brightness of an additional pixel that is located along each line segment. The processor 108 may iteratively compare the magnitude of brightness of the additional pixel along each line segment with the magnitude of brightness of the pixel of the first seed point until the magnitude of brightness of the additional pixel is greater than a predetermined amount. In some embodiments, the predetermined amount may be two or three standard deviations of the magnitude of brightness of the pixel of the first seed point.

Control continues to 816 where, after the location of the outer wall is determined, the processor 108 may determine location of an inner wall of the tube within the image data 112. As described above, the processor may identify a second seed point within the image data 112. The second seed point may be located on an outer wall line. The processor 108 may generate a plurality of inner wall line segments that extend radially inward from the second seed point. The plurality of inner wall line segments extend in a direction that is orthogonal (e.g., 90 degrees) to the outer wall line. Each line segment in the plurality of inner wall line segments terminates at an intersection with the inner wall. To determine the intersection, the processor 108 may identify a magnitude of brightness of a pixel of the second seed point and identify a magnitude of brightness of an additional pixel that is located along each line segment. The processor 108 may iteratively compare the magnitude of brightness of the additional pixel located along each line segment with the magnitude of brightness of the pixel of the second seed point until the magnitude of brightness of the additional pixel is greater than a predetermined amount. In some embodiments, the predetermined amount may be two or three standard deviations of the magnitude of brightness of the pixel of the second seed point.

Control continues to 820 where the processor 108 may generate a three-dimensional structure of the organ based on a centerline, an inner wall line, and an outer wall line. The three-dimensional structure of the organ may be used to segment the organ (e.g., small intestine). The segmented organ may be displayed to a human user on a graphical user interface. The segmented organ may be used to improve the prediction of the likelihood of future clinical outcomes (e.g., surgery, hospitalization, etc.) in patients with Crohn's disease. Once the organ is segmented, the processor 108 may compute a measure of the organ from the image data 112. For example, the measure may include thickness of the bowel wall, diameter of the tube, diameter of the outer wall, length of a diseased section, and contrast assessment. In some embodiments, point cloud data for the inner wall and the outer wall as well as the centerline have been saved off in a database as indicated at 818. Segmentation of the organ and computations of organ measurements can be made from the saved data without having to repeat the imaging process.

Figure 9:
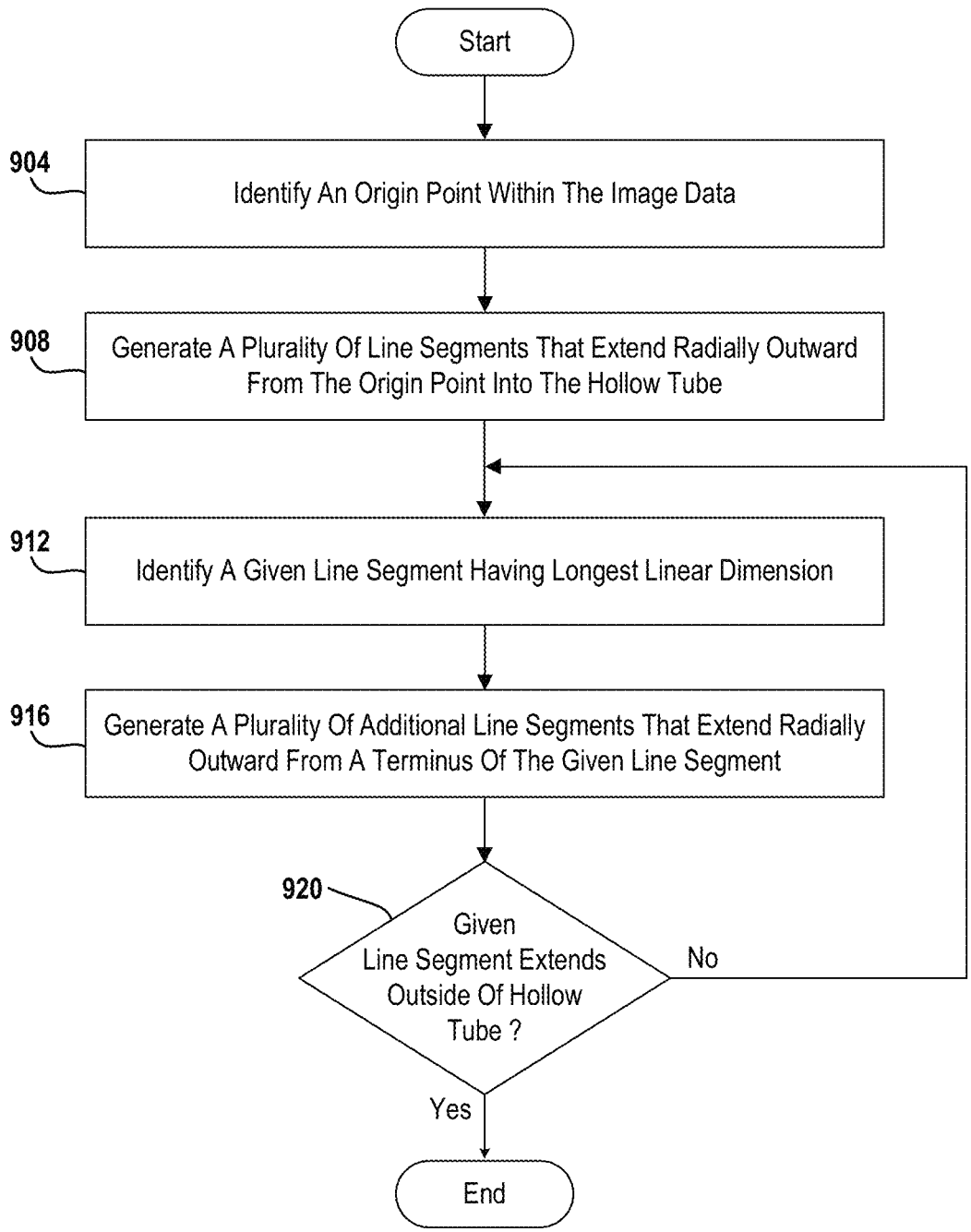
FIG. 9 is a flowchart illustrating an exemplary method for generating a centerline.

Referring now to FIG. 9, a flowchart illustrating an exemplary method for generating the centerline is presented. Control begins at 904, where the processor 108 may identify an origin point within the image data 112. For example, the processor 108 may identify one or more points within the image data 112 that represent an opening of the tube. The opening of the tube may be located at an end where a small intestine intersects with a large intestine. One point in the one or more points may be designated as the origin point. The origin point may be a point that has the highest likelihood of being located substantially near a center of a cross-section of the tube.

Control continues to 908 where the processor 108 may generate a plurality of line segments that extend radially outward from the origin point and into the tube. For example, the plurality of line segments may extend in all directions (e.g., (x, y, z) directions) from the origin point. Each line segment in the plurality of line segments may terminate at an intersection between the corresponding line segment and the inner wall of the tube.

Control continues to 912 where the processor 108 may determine a linear dimension (e.g., length) of each line segment in the plurality of line segments. The processor 108 may identify a given line segment having the longest linear dimension amongst the plurality of line segments. The given line segment is retained.

Control continue to 916 where the processor 108 may generate a plurality of additional line segments that extend radially outward from a terminus of the given line segment and into the tube. The terminus may correspond to an end point of the given line segment. For example, the plurality of additional line segments may extend in all directions (e.g., (x, y, z) directions) from the terminus of the given line segment. Each line segment in the plurality of additional line segments may terminate at an intersection between the corresponding line segment and the inner wall of the tube.

Control continues to 920 where the processor 108 determines if the given line segment extends outside of the tube. If the given line segment does not extend outside of the tube, control returns to 912. Control ends when the given line segment extends outside of the tube. For example, the given line segment may extend outside of the tube at an intersection between the small intestine and the stomach.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A computer-automated method for segmenting image data for an organ of a subject, where the organ is a tube, comprising:
   receiving, by an image processor, image data representing a volume of the subject, such that the image data includes the organ;
   generating, by the image processor, a centerline through of the organ;
   determining, by the image processor, location of an outer wall of the tube within the image data, where the location of the outer wall is determined using the centerline;
   determining, by the image processor, location of an inner wall of the tube within the image data, where the location of the inner wall is determined using the outer wall; and
   computing, by the image processor, a measure of the organ from the image data;
   wherein the location of an outer wall or the location of an inner wall is determined by a) identifying a first seed point within the image data, where the first seed point is located on the centerline;
   b) generating a plurality of inner wall line segments that extend radially outward from the first seed point and that are orthogonal to the centerline, where each line segment in the plurality of inner wall line segments terminates at an intersection with a wall;
   c) identifying a magnitude of brightness of a pixel of the first seed point;
   d) identifying a magnitude of brightness of an additional pixel located along a length of each line segment in the plurality of inner wall line segments, where the additional pixel is moving radially outward from the first seed point; and
   e) repeating step d) until the magnitude of brightness of the additional pixel located along each line segment in the plurality of inner wall line segments is greater than a predetermined amount.

2. The method of claim 1 further comprises capturing the image data using one of computer topography or magnetic resonance imaging.

3. The method of claim 1 wherein generating the centerline further comprises:
   a) identifying an origin point within the image data, where the origin point is located at one end of the tube;
   b) generating a plurality of line segments that extend radially outward from the origin point and into the tube, each line segment in the plurality of line segments terminates at an intersection with the inner wall of the tube;

c) identifying a given line segment having longest linear dimension amongst the plurality of line segments;

d) generating a plurality of additional line segments that extend radially outward from a terminus of the given line segment, where the terminus is located at the intersection with the inner wall, and each line segment in the plurality of additional line segments terminates at the intersection with the inner wall; and e) repeating steps c) and d) until the given line segment extends outside of the tube.

4. The method of claim 3 further comprises joining the given line segment to form a spline curve.

5. The method of claim 3 wherein the origin point is located substantially near a center of a cross section of the tube.

6. The method of claim 1 wherein computing the measure of the organ further comprises at least one of a thickness between the inner wall and the outer wall, diameter of the tube, diameter of the outer wall, length of a diseased section, and contrast assessment.

7. The method of claim 1 wherein determining the location of the outer wall of the tube further comprises:
creating a planar reformation of the volume using the centerline;
for each slice of the volume, converting data for a given slice from a cartesian coordinate to a polar coordinates by generating a plurality of wall line segments that extend radially outward from the first seed point and that are orthogonal to the centerline;
identify candidates that exceed the outer wall magnitude threshold and iteratively add or remove candidates that are proximal to a best fit grid;
transform grid candidates from the polar coordinates to the Cartesian coordinates; and remap the transformed grid points to an original coordinates.

8. The method of claim 1 wherein the predetermined amount is two standard deviations of the magnitude of brightness of the pixel of the first seed point.

9. The method of claim 1 wherein the organ is further defined as a small intestine and an origin point is located at an intersection between the small intestine and a large intestine of the subject.

10. A method for segmenting an organ of a subject, comprising:
a) receiving image data of the organ of the subject, wherein the image data includes at least a small intestine of the subject;
b) identifying an origin point within the image data, wherein the origin point is located at an intersection between the small intestine and a large intestine of the subject;
c) generating a plurality of line segments that extend radially outward from the origin point, each line segment in the plurality of line segments terminates at an intersection with a first boundary of the organ;
d) identifying a given line segment having longest linear dimension amongst the plurality of line segments;
e) identifying a point along the given line segment to serve as a seed location;
f) generating a plurality of additional line segments that extend radially outward from the seed location, each line segment in the plurality of additional line segments terminates at the intersection with the first boundary; and g) repeating steps d) f) until the given line segment extends outside of the organ.

11. The method of claim 10 wherein generating the plurality of line segments and generating the plurality of additional line segments includes using a random walker analysis.

12. The method of claim 10 further comprises capturing the image data using one of computed tomography or magnetic resonance imaging.

13. The method of claim 10 further comprises generating a centerline through the organ by joining the given line segment.

14. The method of claim 13 further comprises determining a location of the first boundary, wherein determining the location includes:
a) identifying a first seed point within the image data, where the first seed point is located on the centerline;
b) generating a plurality of first boundary line segments that extend radially outward from the first seed point and that are orthogonal to the centerline, where each line segment in the plurality of first boundary line segments terminates at an intersection with the first boundary;
c) identifying a magnitude of brightness of a pixel of the first seed point;
d) identifying a magnitude of brightness of an additional pixel located along a length of each line segment in the plurality of first boundary line segments, where the additional pixel is moving radially outward from the first seed point; and
e) repeating step d) until the magnitude of brightness of the additional pixel located along each line segment in the plurality of first boundary line segments is greater than a predetermined amount.

15. The method of claim 14 further comprises determining a location of a second boundary, wherein determining the location includes:
a) identifying a second seed point within the image data, where the second seed point is located on the first boundary;
b) generating a plurality of second boundary line segments that extend radially outward from the second seed point and that are orthogonal to the first boundary, where each line segment in the plurality of second boundary line segments terminates at an intersection with the second boundary;
c) identifying a magnitude of brightness of a pixel of the second seed point;
d) identifying a magnitude of brightness of an additional pixel located along a length of each line segment in the plurality of second boundary line segments, where the additional pixel is moving radially outward from the second seed point; and
e) repeating step d) until the magnitude of brightness of the additional pixel located along each line segment in the plurality of second boundary line segments is greater than the predetermined amount.

16. The method of claim 15 further comprises:
generating a three-dimensional point cloud of the organ based on the centerline, the first boundary, and the second boundary; and
measuring a metric of the organ of the subject.

17. The method of claim 16 wherein the first boundary corresponds to an inner wall of the organ and the second boundary corresponds to an outer wall of the organ.

18. The method of claim 17 wherein the metric of the organ includes at least one of a thickness between the inner wall and an outer wall, diameter of the inner wall, diameter of the outer wall, length of a diseased section, and contrast assessment.

19. A computer-automated method for segmenting image data for an organ of a subject, where the organ is a tube, comprising:

receiving, by an image processor, image data representing a volume of the subject, such that the image data includes the organ;

generating, by the image processor, a centerline through of the organ;

determining, by the image processor, location of an outer wall of the tube within the image data, where the location of the outer wall is determined using the centerline;

determining, by the image processor, location of an inner wall of the tube within the image data, where the location of the inner wall is determined using the outer wall; and computing, by the image processor, a measure of the organ from the image data; wherein the centerline is generated by a) identifying an origin point within the image data, where the origin point is located at one end of the tube;

b) generating a plurality of line segments that extend radially outward from the origin point and into the tube, each line segment in the plurality of line segments terminates at an intersection with the inner wall of the tube;

c) identifying a given line segment having longest linear dimension amongst the plurality of line segments;

d) generating a plurality of additional line segments that extend radially outward from a terminus of the given line segment, where the terminus is located at the intersection with the inner wall, and each line segment in the plurality of additional line segments terminates at the intersection with the inner wall; and e) repeating steps c) and d) until the given line segment extends outside of the tube.

* * * * *